(12) United States Patent  (10) Patent No.: US 7,488,847 B2
Okazoe et al.  (45) Date of Patent: *Feb. 10, 2009

(54) FLUORINATED ADAMANTANE AND ITS DERIVATIVES

(75) Inventors: Takashi Okazoe, Kanagawa (JP); Kunio Watanabe, Kanagawa (JP); Masahiro Ito, Kanagawa (JP); Eisuke Murotani, Kanagawa (JP); Kazuya Oharu, Kanagawa (JP); Shu-zhong Wang, Kanagawa (JP); Taiki Hoshino, Kanagawa (JP); Kimiaki Kashiwagi, Kanagawa (JP)

(73) Assignee: Asahi Glass Company, Limited, Tokyo (JP)

( * ) Notice: Subject to any disclaimer, the term of this patent is extended or adjusted under 35 U.S.C. 154(b) by 594 days.

This patent is subject to a terminal disclaimer.

(21) Appl. No.: 11/153,438

(22) Filed: Jun. 16, 2005

(65) Prior Publication Data

US 2005/0288528 A1 Dec. 29, 2005

Related U.S. Application Data

(63) Continuation-in-part of application No. 11/143,978, filed on Jun. 3, 2005, now Pat. No. 7,314,952, which is a continuation of application No. PCT/JP03/15879, filed on Dec. 11, 2003.

(30) Foreign Application Priority Data

| Dec. 11, 2002 | (JP) | ............................ 2002-359471 |
| Jun. 16, 2004 | (JP) | ............................ 2004-178330 |
| Jun. 16, 2004 | (JP) | ............................ 2004-178331 |

(51) Int. Cl.
 *C07C 63/00* (2006.01)
(52) U.S. Cl. .................................................. 562/850
(58) Field of Classification Search ........................ None
 See application file for complete search history.

(56) References Cited

U.S. PATENT DOCUMENTS

| 4,284,558 | A | 8/1981 | Barton et al. |
| 7,084,295 | B2 | 8/2006 | Tanaka et al. |
| 2005/0288528 | A1 | 12/2005 | Okazoe et al. |

FOREIGN PATENT DOCUMENTS

| CA | 1064475 | 10/1979 |
| EP | 1 460 057 | 9/2004 |
| JP | 51-4102 | 1/1976 |
| JP | 57-79187 | 5/1982 |
| JP | 4-502319 | 4/1992 |
| JP | 9-43848 | 2/1997 |
| JP | 2001-60583 | 3/2001 |
| JP | 2001-109156 | 4/2001 |
| JP | 2003-280205 | 10/2003 |
| JP | 2004-123687 | 4/2004 |
| JP | 2005-23066 | 1/2005 |
| JP | 2005-89363 | 4/2005 |
| WO | WO 00/56694 | 9/2000 |
| WO | WO 03/055841 | 7/2003 |
| WO | WO 03/055841 | 10/2003 |
| WO | WO 2004/050725 | 6/2004 |
| WO | WO 2004/052832 A1 | 6/2004 |

OTHER PUBLICATIONS

Muthiah Manoharan, et al., "Lipidic Nucleic Acids", Tetrahedron Letters, vol. 36, No. 21, 1995, pp. 3651-3654.
U.S. Appl. No. 11/611,183, filed Dec. 15, 2006, Oharu, et al.
U.S. Appl. No. 11/567,391, filed Dec. 6, 2006, Wang, et al.
Fărcaşiu et al, J. Am. Chem. Soc., 1985, vol. 107, pp. 5717-5722.
Adcock et al, J. Org. Chem., 1996, vol. 61, pp. 5073-5076.

(Continued)

*Primary Examiner*—Paul A Zucker
(74) *Attorney, Agent, or Firm*—Oblon, Spivak, McClelland, Maier & Neustadt, P.C.

(57) ABSTRACT

The present invention provides a process A1 for producing a compound (5A), which comprises fluorinating a compound (3A-1) by liquid phase fluorination to a compound (4A-1), followed by a decomposition reaction of an ester bond; a process A2 for producing a compound (5A), which comprises fluorinating a compound (3A-2) by liquid phase fluorination to a compound (4A-2), followed by a decomposition reaction of an ester bond; and a process B for producing a compound (5B), which comprises fluorinating a compound (3B) by liquid phase fluorination to a compound (4B), followed by hydrolysis or alcoholysis. Further, the present invention provides a compound (5A) wherein n is 2 to 4, and a compound (5B) wherein n is 3 or 4.

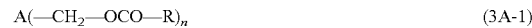

(3A-1)

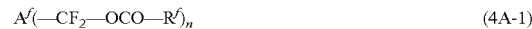

(4A-1)

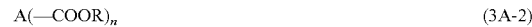

(3A-2)

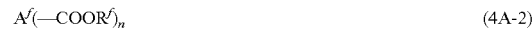

(4A-2)

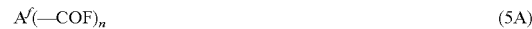

(5A)

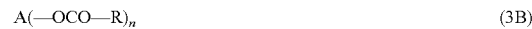

(3B)

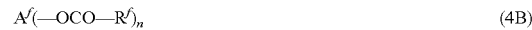

(4B)

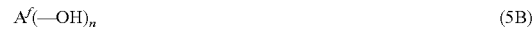

(5B)

provided that the carbon atom in adamantane to which —OCO—$R^f$ is bonded, is a tertiary carbon atom, A is a n-valent group having n hydrogen atoms in adamantane converted to connecting bonds, R is a fluorinated monovalent organic group, n is an integer of from 1 to 4, $A^f$ is a group having at least one of hydrogen atoms in the group A substituted by a fluorine atom, and $R^f$ is a fluorinated monovalent organic group.

9 Claims, No Drawings

OTHER PUBLICATIONS

Adcock et al, J. Org. Chem., 1995, vol. 60, pp. 1999-2002.

Adcock et al, J. Org. Chem., 1992, vol. 57, pp. 4297-4300.

Douglas J. Raber, et al., "Structure elucidation with Lanthanide-Induced Shifts 5. Evaluation of the Binding Ability of Various Functional Groups", Monatshefte Fuer Chemie, 111(1), XP-008063999, 1980, pp. 43-52.

T. William Bentley, et al., "Weakly Nucleophilic Leaving Groups. Solvolyses of 1-Adamantyl and t-Butyl Heptafluorobutyrates and Trifluoroacetates", Journal of the Chemical Society, Perkin Transactions 2, (8), XP-008063967, 1989, pp. 1055-1060.

V. A. Soloshonok, et al., "Reaction of 3, 7-dimethylenebicyclo (3.3.1) nonane with pyridinium perfluorocarboxylates", Zhurnal Organicheskoi Khimii, 25(10), 1989, XP-02380189, pp. 2242-2243 (with English Abstract).

D. T. Stoelting, et al., "Solvolysis of 1-(3-noradamantyl)-2-methylpropyl and 1-(3-noradamantyl)-2, 2-dimethylpropyl pentamethylbenzenesulfonates", Croatica Chemica Acta, 65(3), 1992, XP-02380190, pp. 517-538.

Pavel A. Krasutsky, et al., "Observation of a Stable Carbocation in a Consecutive Criegee Rearrangement with Trifluoroperacetic Acid", Journal of Organic Chemistry, 65(13), XP-002380168, 2000, pp. 3926-3933.

Stephen R. Jones, et al., "Mechanism of Oxidation of Saturated Hydrocarbons by Lead (IV), Cobalt (III), and Manganese (III) Trifluoroacetates", Journal of the Chemical Society, Chemical Communications, (11), XP-008063962, 1976, pp. 385-386.

Pavel A. Krasutsky, et al., "Heterolytic decarboxylation involving acyltrifluoroacetyl peroxide intermediates", Tetrahedron Letters, 43(48), XP-002380169, 2002, pp. 8687-8691.

James L. Adcock, et al., "Aerosol fluorination of 1-Chloroadamantane, 2-Chloroadamantane, and Methyl 1-Adamantylacetate: A Novel Synthetic Approach to 1-and 2-substituted Hydryl-, Methyl-, and (Difluoromethyl)-F-adamantanes", Journal of Organic Chemistry, 57(17), XP-002380170, 1992, pp. 4749-4752.

Oldrich Paleta, et al., "Synthesis of 1-Adamantanol 2, 3, 3-Trifluoroacrylate", Journal of Fluorine Chemistry, 47(3), XP-002380172, 1990, pp. 435-440.

Klaus Banert, et al., "Nucleophile Substitution bei 4, 4-Dimethyl-2-adamantyl-Substraten: Rueckseitenangriff bei 2-Adamantan-Derivaten", Chemische Berichte, 119(12), XP-008064006, 1986, p. 3826-3841 (with English Abstract).

Neil A. Marron, et al., "A Direct Photochemical Synthesis of 1, 2-Disubstituted Adamantanes", Synthetic Communications, 7(8), XP-008063974, 1977, pp. 515-520.

Helmut Duddeck, et al., "Synthesen und $^{13}$C-NMR-spektroskopische Untersuchungen trifluormethylsubstituierter Adamantane", Liebigs Ann. Chem., No. 3, 1985, pp. 545-554 (with English Abstract).

U.S. Appl. No. 11/143,978, filed Jun. 3, 2005, Okazoe, et al.

U.S. Appl. No. 11/153,438, filed Jun. 16, 2005, Okazoe, et al.

U.S. Appl. No. 12/091,846, filed Apr. 28, 2008, Wang, et al.

FLUORINATED ADAMANTANE AND ITS DERIVATIVES

CROSS REFERENCE TO A RELATED APPLICATION

The present application is a continuation-in-part of U.S. application Ser. No. 11/143,978, filed Jun. 3, 2005, which is a continuation of International Application PCT/JP03/15879, filed Dec. 11, 2003.

BACKGROUND OF THE INVENTION

1. Field of the Invention

The present invention relates to novel fluorinated adamantane and its derivatives, and processes for their production.

2. Discussion of Background

A method for introducing fluorine into the adamantane skeleton by aerosol fluorination, has been reported. For example, in J. Org. Chem., 1995, 60, 1999 2002, J. Org. Chem., 1996, 61, 5073-5076 (Document 1) and J. Org. Chem., 1992, 57, 4297-4300, a method for producing fluorinated adamantane having one or two hydroxyl groups and hydrogen atoms, is reported. In the above Document 1, a method for producing perfluorinated adamantane having one hydroxyl group, is also reported. However, by such an aerosol fluorination method, the yield is low, and it is difficult to practically use it for an industrial purpose.

JP-A-57-79187 discloses that perfluorinated adamantane having one —COF group, is contained in the product obtained by electrochemically fluorinating 1-adamantane methanol.

EP1460057A discloses a general formula which covers fluorinated adamantane having from one to four acryloyloxy groups, but no method for obtaining the starting material is disclosed.

WO2004/050725 discloses a polymer of perfluorinated adamantane having one acryloyloxy group.

SUMMARY OF THE INVENTION

The present inventors have considered that fluorinated adamantane derivatives may possibly be materials which are excellent in transmittance of light having a shorter wavelength and excellent in etching resistance and which can be applied to finner photolithography. Namely, it is an object of the present invention to provide novel fluorinated adamantane which can be provided by an economically advantageous method from readily available materials.

Such fluorinated adamantane can be converted to derivatives by utilizing the reactivity of e.g. a —OH group or a —COF group. The compounds derived from the fluorinated adamantane can be utilized as etching resistant thin film materials which can be materials excellent in both etching resistance and transmittance to light in the photolithography employing a laser beam with a short wavelength.

The present invention provides the following:

(1) A process for producing a compound of the following formula (5A), which comprises fluorinating a compound of the following formula (3A-1) by liquid phase fluorination to a compound of the following formula (4A-1), and then carrying out a decomposition reaction of an ester bond in the compound of the formula (4A-1):

 (3A-1)

 (4A-1)

 (5A)

provided that the symbols in the formulae have the following meanings:

A: a n-valent group having n hydrogen atoms in adamantane converted to connecting bonds,
R: a fluorinated monovalent organic group,
n: an integer of from 1 to 4,
$A^f$: a group having at least one of hydrogen atoms in the group A substituted by a fluorine atom,
$R^f$: a fluorinated monovalent organic group.

(2) A process for producing a compound of the following formula (5A), which comprises fluorinating a compound of the following formula (3A-2) by liquid phase fluorination to a compound of the following formula (4A-2), and then carrying out a decomposition reaction of an ester bond in the compound of the formula (4A-2):

 (3A-2)

 (4A-2)

 (5A)

provided that the symbols in the formulae have the following meanings:

A: a n-valent group having n hydrogen atoms in adamantane converted to connecting bonds,
R: a fluorinated monovalent organic group,
n: an integer of from 1 to 4,
$A^f$: a group having at least one of hydrogen atoms in the group A substituted by a fluorine atom,
$R^f$: a fluorinated monovalent organic group.

(3) A process for producing a compound of the following formula (5B), which comprises fluorinating a compound of the following formula (3B) by liquid phase fluorination to a compound of the following formula (4B), and then carrying out hydrolysis or alcoholysis of the compound of the formula (4B):

 (3B)

 (4B)

 (5B)

provided that the carbon atoms in adamantane to which —OCO—R or —OCO—$R^f$ is bonded, are tertiary carbon atoms, and the symbols in the formulae have the following meanings:

A: a n-valent group having n hydrogen atoms in adamantane converted to connecting bonds,
R: a fluorinated monovalent organic group,
n: an integer of from 1 to 4,
$A^f$: a group having at least one of hydrogen atoms in the group A substituted by a fluorine atom,
$R^f$: a fluorinated monovalent organic group.

(4) A compound of the following formula (5a'):

 (5a')

wherein $A^f$: a group having at least one of hydrogen atoms in a n-valent group A having n hydrogen atoms in adamantane converted to connecting bonds, substituted by a fluorine atom,
n: an integer of from 2 to 4.

(5) A compound of the following formula (5b'):

 (5b')

wherein $A^f$: a group having at least one of hydrogen atoms in a n-valent group A having n hydrogen atoms in adamantane converted to connecting bonds, substituted by a fluorine atom, n: 3 or 4.

(6) A process for producing an acrylate of the following formula (6), which comprises reacting a compound of the following formula (5B) with a compound of the following formula (10):

$$A^f(\text{—OH})_n \quad (5B)$$

$$CH_2\!=\!CR^1COX^{11} \quad (10)$$

$$A^f(OCOCR^1\!=\!CH_2)_m(\text{—OH})_{n\text{-}m} \quad (6)$$

wherein $A^f$ and n are as defined above, $X^{11}$ is a hydroxyl group or a halogen atom, $R^1$ is a hydrogen atom or a methyl group, and m is an integer of from 1 to 4, provided $n \geq m$.

DETAILED DESCRIPTION OF THE PREFERRED EMBODIMENTS

In this specification, the monovalent organic group means a monovalent group essentially containing carbon atom(s). The monovalent organic group is preferably a monovalent organic group having C—H portions and may, for example, be an alkyl group or an alkyl group having an etheric oxygen atom inserted between carbon-carbon atoms.

In this specification, "fluorinated" means that some or all of portions which may be fluorinated, in a group to be fluorinated, are fluorinated. Further, "perfluorinated" means substantially all of portions which may be fluorinated, in a group to be fluorinated, are fluorinated.

The perfluorinated monovalent organic group may, for example, be a perfluoroalkyl group and may, specifically be —$CF_2CF_3$, —$CF_2CF_2CF_3$, —$CF_2CF_2CF_2CF_3$, —$CF(CF_3)_2$, —$CF_2CF(CF_3)_2$, —$CF(CF_3)CF_2CF_3$ or —$C(CF_3)_3$. The perfluorinated group containing an etheric oxygen atom may, for example, be —$CF(CF_3)[OCF_2CF\ (CF_3)]_bOCF_2CF_2CF_3$ (wherein b is an integer of 0 or more, preferably an integer of 0 or from 1 to 5) or —$(CF_2)_dOCF_3$ (wherein d is an integer of at least 1, preferably an integer of from 1 to 8).

In the present invention, the compound (5A) which is fluorinated adamantane having a —COF group, is produced by the following process A-1 or A-2.

Process A-1: A process for producing the compound (5A) which comprises fluorinating the compound (3A-1) by liquid phase fluorination to a compound (4A-1), followed by a decomposition reaction of an ester bond:

$$A(\text{—}CH_2\text{—}OCO\text{—}R)_n \quad (3A\text{-}1)$$

$$A^f(\text{—}CF_2\text{—}OCO\text{—}R^f)_n \quad (4A\text{-}1)$$

$$A^f(\text{—}COF)_n \quad (5A)$$

Process A-2: A process for producing the compound (5A) which comprises fluorinating the compound (3A-2) by liquid phase fluorination to a compound (4A-2), followed by a decomposition reaction of an ester bond:

$$A(\text{—}COOR)_n \quad (3A\text{-}2)$$

$$A^f(\text{—}COOR^f)_n \quad (4A\text{-}2)$$

$$A^f(\text{—}COF)_n \quad (5A)$$

The compound (5B) which is fluorinated adamantane having a —OH group, is produced by the following process B.

Process B: A process which comprises fluorinating the compound (3B) by liquid phase fluorination to a compound (4B), and then carrying out hydrolysis or alcoholysis of the compound (4B):

$$A(\text{—}OCO\text{—}R)_n \quad (3B)$$

$$A^f(\text{—}OCO\text{—}R^f)_n \quad (4B)$$

$$A^f(\text{—}OH)_n \quad (5B)$$

Here, adamantane is a compound represented by the following formula:

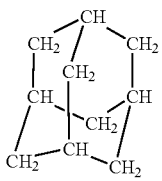

In the above formulae, n represents the number of bonds bonded to adamantane, and it is an integer of from 1 to 4, unless otherwise specified. When n is 2 or more, the positions of the substituents bonded to A or $A^f$ are preferably different carbon atoms. A compound wherein n is 2 or more can be produced in good yield, as the liquid phase fluorination reaction can easily be controlled.

In the formulae, A represents a n-valent group having n hydrogen atoms in the above adamantane converted to connecting bonds. A hydrogen atom which can be converted to a connecting bond of adamantane may be a hydrogen atom bonded to a secondary carbon atom, or a hydrogen atom bonded to a tertiary carbon atom, preferably one bonded to a tertiary carbon atom. However, a hydrogen atom which can be a connecting bond of adamantane in the formulae (3B) to (5B) is one bonded to a tertiary carbon atom.

$A^f$ in the formulae is a group having at least one of hydrogen atoms in the group A substituted by a fluorine atom. $A^f$ is preferably a group having at least 50% of hydrogen atoms in A substituted by fluorine atoms, particularly preferably a group having at least 90% substituted by fluorine atoms, most preferably a perfluoro group having 100% substituted (a case where A is a perfluoro group, is represented by $A^F$). Namely, $A^f$ is preferably $A^F$.

R in the formulae is a fluorinated monovalent organic group, preferably a fluorinated monovalent saturated hydrocarbon group or a fluorinated monovalent saturated hydrocarbon group having an etheric oxygen atom, particularly preferably a fluorinated alkyl group or a fluorinated alkyl group containing an etheric oxygen atom. The carbon number of R is preferably from 2 to 20, particularly preferably from 2 to 10. R is particularly preferably a polyfluoroalkyl group or a polyfluoroalkyl group containing an etheric oxygen atom. Further, R is preferably a perfluorinated group. R may, for example, be a perfluoroalkyl group, a perfluoro(partially chloroalkyl group), a perfluoro(partially bromoalkyl group) or a perfluoroalkyl group containing an etheric oxygen atom, preferably a perfluoroalkyl group or a perfluoroalkyl group containing an etheric oxygen atom, particularly preferably such a group having from 2 to 20 carbon atoms.

$R^f$ is a fluorinated monovalent organic group, and a preferred mode of such a group is the same as R. In a case where R is a perfluoro monovalent organic group, $R^f$ is the same group as R. When $R^f$ is a perfluoro monovalent organic group, it is represented by $R^F$.

The liquid phase fluorination in process A-1, A-2 and B is a method for a reaction with fluorine ($F_2$) in a liquid phase. By such liquid phase fluorination, the fluorination reaction can be carried out in good yield. The fluorine content of the substrate for fluorination is preferably from 20 to 60 mass %, particularly preferably from 25 to 55 mass %, whereby the solubility in the liquid phase will be improved, and the operation efficiency of the reaction and the reaction yield will be improved. The molecular weight of the substrate for fluorination is preferably from 200 to 1,100, particularly preferably from 300 to 800. When the lower limit of the molecular weight of the substrate for fluorination is 200 (preferably 300), there is a merit such that the decomposition reaction by a gas phase fluorination reaction can be avoided. In a case where the upper limit of the molecular weight is 1,100 (preferably 800), handling of the compound or purification of the product will be easy.

As the liquid phase for the liquid phase fluorination, it is preferred to employ the substrate for fluorination or the product, or a solvent which will not be involved in the reaction. As such a solvent, a solvent capable of dissolving at least 1 mass % of the substrate for fluorination, particularly a solvent capable of dissolving at least 5 mass %, is preferred. As the solvent, a known solvent to be used as a solvent for liquid phase fluorination may, for example, be used. Such a known solvent may, for example, be a chlorofluorocarbon such as $CF_2ClCFCl_2$, perfluorotributylamine, or a fluorocarbon such as perfluoro(2-butyltetrahydrofuran). The amount of the solvent is preferably at least 5 times, particularly preferably from $1\times10^1$ to $1\times10^5$ times by mass, relative to the total mass of the substrate for fluorination. The fluorination reaction is preferably carried out by a batch system or a continuous system. As fluorine, it is preferred to employ 100% fluorine gas or fluorine gas diluted with an inert gas. As such an inert gas, nitrogen gas is preferred. When diluted with an inert gas, the amount of the fluorine gas in the inert gas is preferably at least 10 vol %, particularly preferably at least 20 vol %, from the viewpoint of the efficiency.

In the liquid phase fluorination, the amount of fluorine is adjusted to be preferably at least 1.05 times by equivalent, particularly preferably at least 2 times by equivalent, relative to hydrogen atoms present in the substrate for fluorination. It is preferred that fluorine is preliminarily dissolved in a sufficient amount in the solvent for fluorination reaction to be used at the initial stage of the reaction.

The reaction temperature for the liquid phase fluorination reaction is preferably from −50° C. to +100° C., particularly preferably from −20° C. to +50° C. The reaction pressure for the fluorination reaction is preferably from atmospheric pressure to 2 MPa. In the liquid phase fluorination reaction, it is preferred to add e.g. benzene or toluene to the system or to conduct irradiation of ultraviolet rays.

In the liquid phase fluorination reaction, it is preferred that at least 95% of the total number of hydrogen atoms is substituted, particularly preferably perfluorinated. However, in the present invention, a partially fluorinated compound wherein hydrogen atoms are still present, may also be useful depending upon the particularly purpose.

In the liquid phase fluorination, a HF-scavenger (preferably NaF) may be permitted to be present. HF may be discharged out of the reaction system as accompanied with an inert gas such as nitrogen gas and then subjected to alkali treatment. In a case where the reaction product of the fluorination reaction is to be purified, a distillation method is preferred.

The decomposition reaction of an ester bond in process A-1 and process A-2 is preferably a thermal decomposition reaction or a decomposition reaction carried out in the presence of a nucleophilic agent or an electrophilic agent.

The thermal decomposition reaction is preferably carried out by a method of heating in a liquid phase. The product may be withdrawn all at once from the reactor after completion of the reaction. Otherwise, the reaction may be carried out while the product is being withdrawn by distillation. The reaction temperature for the decomposition reaction is preferably from 50 to 300° C., particularly preferably from 100 to 250° C. The reaction pressure is not limited. The decomposition reaction in a liquid phase is preferably carried out in the absence of a solvent. In a case where a solvent is used, the amount of the solvent relative to the substrate for the decomposition reaction is preferably from 0.1 to 10 times by mass. The reaction is preferably carried out, while distillation is carried out by a reaction apparatus equipped with a distillation column.

As the nucleophilic agent to be used for the decomposition reaction of an ester bond, $F^-$ is preferred, such as $F^-$ derived from NaF, $NaHF_2$, KF or CsF. From the viewpoint of the economical efficiency, NaF is preferred, and from the viewpoint of the reaction activity, KF is particularly preferred. The amount of the nucleophilic agent is preferably from 1 to 500 mol %, particularly preferably from 1 to 100 mol %, especially preferably from 5 to 50 mol %, based on the substrate. The lower limit of the reaction temperature is preferably −30° C., and the upper limit is preferably from −20° C. to 250° C.

For the liquid phase fluorination in process B, the method in process A-1 and process A-2 may be employed as it is. The hydrolysis or alcoholysis in process B is preferably a decomposition reaction to be carried out in the presence of a compound of the formula $R^H$—OH (wherein $R^H$ is a hydrogen atom or a monovalent hydrocarbon group). In a case where $R^H$ is a hydrogen atom, the reaction will be hydrolysis, and in a case where $R^H$ is a monovalent hydrocarbon group, the reaction will be alcoholysis.

In a case where the compound of the formula $R^H$—OH is an alcohol, it is preferably a primary or secondary alcohol, particularly preferably a cycloalkanol. As a specific example of the primary alcohol, methanol, ethanol, 2-ethylhexyl alcohol or octanol may be mentioned, and as a specific example of the secondary alcohol, 2-propanol, 2-butanol or cyclohexanol may, for example, be mentioned. A $C_{6-10}$ alcohol is preferred, and it is particularly preferred to select it from alcohols having boiling points higher than the product of the decomposition reaction.

The decomposition reaction is preferably carried out under an acidic or basic condition. As an acid to make the acidic condition, hydrochloric acid or sulfuric acid is, for example, preferred. As a base to make the basic condition, an alkali metal hydroxide (such as NaOH, KOH or CsOH) or an alkaline earth metal hydroxide, is preferred, and NaOH is particularly preferred. The reaction temperature is preferably from 50 to 300° C., particularly preferably from 100 to 250° C. The reaction pressure is not particularly limited.

The decomposition reaction of the compound (4B) may be carried out in the presence of a solvent. When a solvent is to be used, its amount is preferably from 0.1 to 10 times by mass relative to the compound (4B). In a case where the compound of the formula $R^H$—OH is used in an excess amount, such a compound may serve also as a solvent.

The product of the decomposition reaction is preferably purified by a distillation method. Otherwise, the decomposition reaction may be carried out in a reactive distillation system, so that the reaction is carried out while the product is being withdrawn.

The compound (3A-1) as the starting material, can be obtained by esterifying adamantane having one to four hydroxylmethyl groups. The compound (3B) can be obtained by esterifying adamantane having one to four hydroxyl groups.

The following compounds may be mentioned as examples of the compound (3A-1) in process A-1.

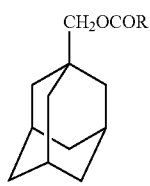
(3A-11)

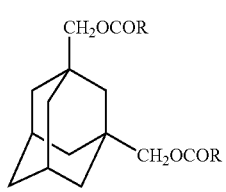
(3A-12)

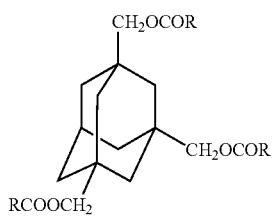
(3A-13)

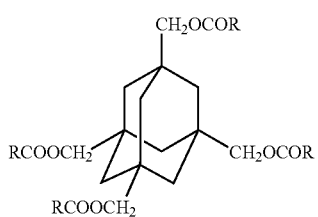
(3A-14)

The following compounds may be mentioned as examples of the compound (3A-2) in process A-2.

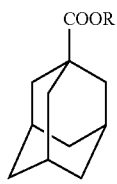
(3A-21)

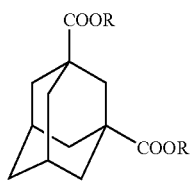
(3A-22)

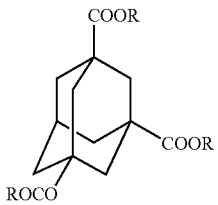
(3A-23)

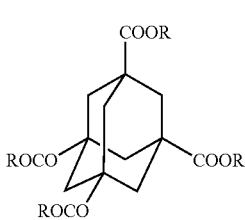
(3A-24)

The following compounds may be mentioned as examples of the compound (3B) in process B.

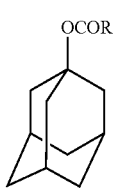
(3B-1)

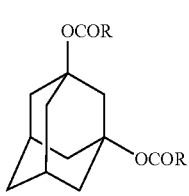
(3B-2)

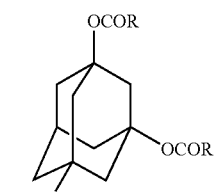
(3B-3)

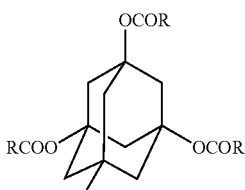
(3B-4)

The following compounds may be mentioned as examples of the compound (5A) to be provided by the process of the present invention.

The following compounds may be mentioned as examples of the compound (5B) to be provided by the process of the present invention.

(5a-1), (5a-2), (5a-3), (5a-4): [fluorinated adamantane structures with COF groups]

(5b-1), (5b-2), (5b-3), (5b-4): [fluorinated adamantane structures with OH groups]

In the above examples of the compound (5A) and the compound (5B), some of fluorine atoms bonded to carbon atoms forming the adamantane skeleton, may be substituted by hydrogen atoms.

Some of the compound (5A) and the compound (5B) are novel compounds provided for the first time by a liquid phase fluorination reaction. Namely, the present invention provides the following compound (5a') which is fluorinated adamantane having from 2 to 4 —COF groups. Here, $A^f$ is as defined above, and is preferably a perfluorinated group ($A^F$). In the compound (5a'), n is an integer of from 2 to 4, and in the compound (5b'), n is 3 or 4.

$$A^f(-COF)_n \tag{5a'}$$

As the compound (5a'), the above-mentioned compound (5a-2), compound (5a-3) or compound (5a-4) is preferred.

Further, the present invention provides the following compound (5b') which is fluorinated adamantane having 3 or 4 —OH groups.

$$A^f(-OH)_n \tag{5b'}$$

The compound (5b') may, for example, be the above compound (5b-3) or compound (5b-4).

The compound (5A) obtained by the process of the present invention may be converted to various derivatives by utilizing the reactivity of the —COF group. For example, a compound obtained by an esterification reaction of the —COF group with propen-2-ol, is a vinyl ester useful as a comonomer for an etching resistant polymer. Further, a compound having 2 to 4 —COF groups is useful as a crosslinking agent or a polymerizable monomer, or as a starting material thereof.

The compound (5B) may be led to an acrylate useful as a comonomer for an etching resistant polymer, by an esterification reaction of a hydroxyl group to form acryloyl or methacryloyl (hereinafter acryloyl and methacryloyl will generally be referred to as (meth)acryloyl). The conversion to the acrylate can be carried out by reacting the compound (5B) with the following compound (10). Here, $R^1$, $A^f$ and n in the formulae are as defined above, and m is an integer of from 1 to 4, provided n≧m. $X^{11}$ is a hydroxyl group or a halogen atom, preferably a chlorine atom or a fluorine atom. A case where n and m are the same number, means a case where hydroxyl groups present in the compound (5B) are all esterified, and no hydroxyl group is present in the compound (6).

$$CH_2=CR^1COX^{11} \tag{10}$$

$$A^f(OCOCR^1=CH_2)_m(-OH)_{n-m} \tag{6}$$

The following compounds may be mentioned as specific examples of the compound (10).

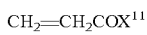

$CH_2$=$CH_2COX^{11}$

$CH_2$=$CH(CH_3)COX^{11}$

The reaction of the compound (5B) with the compound (10) can be carried out by the following methods 1 to 4.

Method 1: A method of subjecting the compound (5B) and the compound (10) to azeotropic dehydration under reflux of a solvent.

Method 2: A method of subjecting the compound (5B) and the compound (10) to dehydration esterification in the presence of a solvent.

Method 3: A method of subjecting the compound (5B) and the compound (10) to an esterification reaction in the presence of a base.

Method 4: A method of converting a hydroxyl group of the compound (5B) to an alkoxide, followed by a reaction with the compound (10) wherein $X^{11}$ is a chlorine atom.

As the solvent in method 1, toluene or xylene is, for example, preferred. The reaction temperature is preferably from −78° C. to 200° C. The reaction pressure is preferably from 0.1 to 10 MPa (gauge pressure), and the reaction time is preferably from 1 to 24 hours, particularly preferably from 3 to 6 hours. The amount of the solvent is preferably at least such an amount that the compound (5B) reaches a saturation concentration, particularly preferably such an amount that the concentration of the compound (5B) becomes from 0.5 to 1.0 mol/liter.

As the dehydrating agent in method 2, molecular sieve, anhydrous sodium sulfate, anhydrous magnesium sulfate, or an acidic dehydrating agent such as phosphoric anhydride, is preferred. The solvent may, for example, be an ether solvent such as diethyl ether, tetrahydrofuran or dioxane; an aliphatic hydrocarbon solvent such as hexane, heptane or octane; or an aromatic hydrocarbon solvent such as benzene, toluene or xylene. The reaction temperature for the dehydration esterification reaction is preferably from 25° C. to the boiling point of the solvent under the reaction pressure, particularly preferably from −78 to 200° C. The reaction pressure is preferably from 0.1 to 10 MPa, particularly preferably atmospheric pressure. The reaction time is preferably from 1 to 24 hours, particularly preferably from 3 to 6 hours. The amount of the solvent is preferably such an amount that the concentration of the compound (5B) becomes from 0.5 to 1.0 mol/liter.

As the base in method 3, trimethylamine, triethylamine, pyridine or N,N-dimethylaniline may, for example, be mentioned. In the reaction, the solvent may or may not be used. In a case where a solvent is to be used, it may, for example, be a halogenated hydrocarbon such as dichloromethane, chloroform, carbon tetrachloride or 1,2-dichloroethane; an ether solvent such as diethyl ether, tetrahydrofuran or dioxane; an aliphatic hydrocarbon solvent such as hexane, heptane or octane; or an aromatic hydrocarbon solvent such as benzene, toluene or xylene. The amount of the solvent is preferably such an amount that the concentration of the compound (5B) becomes from 0.5 to 1.0 mol/liter. The reaction temperature is preferably from −78° C. to +100° C., particularly preferably from −78° C. to +25° C. The reaction pressure is preferably from 0.1 to 10 MPa (gauge pressure). The reaction time is preferably from 1 to 24 hours, particularly preferably from 1 to 3 hours.

In method 4, the method of converting a hydroxyl group of the compound (5B) to an alkoxide, is preferably carried out by a method of reacting the compound (5B) with an alkoxylating agent. The alkoxylating agent may, for example, be lithium metal, sodium metal, potassium metal, n-butyllithium, sec-butyllithium, tert-butyllithium, sodium hydroxide, sodium hydride, sodium borohydride, or lithium aluminum hydride. In such a reaction, it is preferred to use a solvent for the reaction. Examples of the solvent for the reaction may be those similar to the examples given in method 2.

In method 4, a solvent may or may not be used for the reaction of the alkoxide of the compound (5B) with the compound (10) wherein $X^{11}$ is a chlorine atom. In a case where a solvent for the reaction is to be used, a solvent similar to the solvent in the conversion reaction of an alkoxide may be used. The amount of the solvent for the reaction is preferably such an amount that the concentration of the compound (10) becomes from 0.5 to 1.0 mol/liter. The reaction temperature is preferably from −78° C. to 100° C., particularly preferably from −78° C. to 25° C. The reaction pressure is preferably from 0.1 to 10 MPa (gauge pressure). The reaction time is preferably from 1 to 24 hours, particularly preferably from 1 to 3 hours.

The following compounds may be mentioned as examples of the acrylic acid derivative obtained by conversion of the compound (5B). Here, in the following formulae, A is a (meth)acryloyl group, and some of fluorine atoms bonded to carbon atoms in the adamantane skeleton may be substituted by hydrogen atoms.

Examples of the derivative having one (meth)acryloyl group:

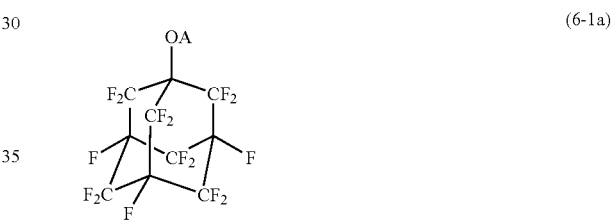

(6-1a)

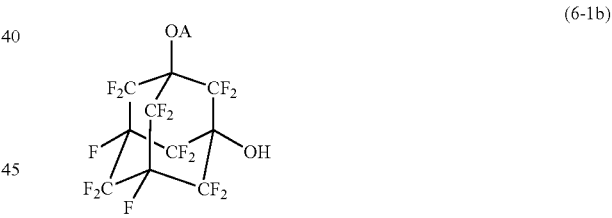

(6-1b)

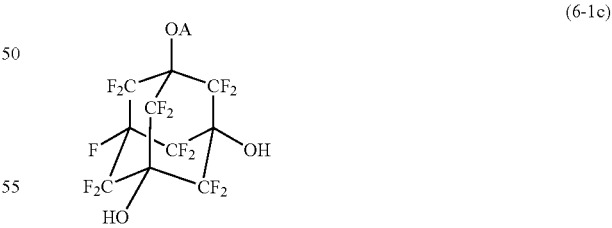

(6-1c)

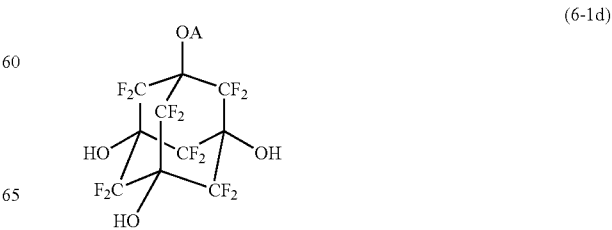

(6-1d)

Examples of the derivative having two (meth)acryloyl groups:

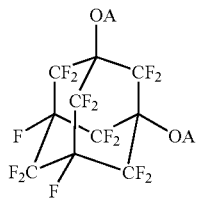
(6-2a)

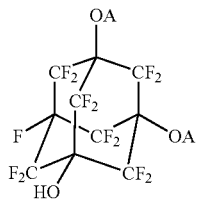
(6-2b)

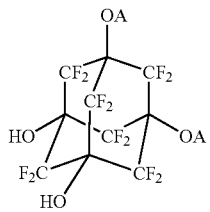
(6-2c)

Examples of the derivative having three or four (meth)acryloyl groups:

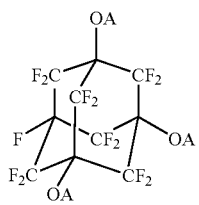
(6-3a)

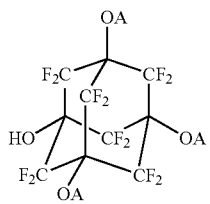
(6-4a)

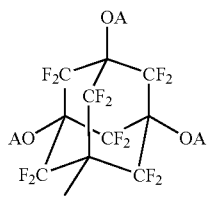
(6-4b)

Such a (meth)acrylic acid derivative has a (meth)acryloyl group as a polymerizable group, and it may be polymerized alone or with another comonomer to obtain a polymer. The type of the comonomer may optionally be changed depending upon the application of the polymer. The obtained polymer has a rigid fluorinated adamantane structure in its side chains, and it can be a hard polymer with little volume change. Further, such a polymer is also a polymer having various functions derived from fluorine atoms. Accordingly, such a polymer is useful as a material for fine photolithography or for an optical adhesive or the like.

Further, a polymer obtained by polymerization of a (meth) acrylic acid derivative having a partially fluorinated adamantane skeleton, has a refractive index different from the perfluorinated polymer and thus can be a polymer having a desired refractive index depending upon the purpose. Further, by introducing hydrogen atoms, the solubility of the polymer in a solvent can also be adjusted.

In a case where a polymer obtained from the adamantane derivative of the present invention is used as a material for photolithography, it can be a material having both a high level of etching resistance and light transmittance. Namely, with an adamantane skeleton having a structure wherein cyclic compounds are bonded to each other, even if part of bonds is broken by a laser beam, the compound hardly undergoes decomposition and remains to be stable. Further, the adamantane derivatives of the present invention essentially have C—F structures, and such structures are less susceptible to decomposition than C—H structures, and carbon-carbon bonds will also be stronger.

Now, the present invention will be described in further detail with reference to Examples. However, it should be understood that the present invention is by no means restricted thereto. In Examples, 1,1,2-trichloro-1,2,2-trifluoroethane will be referred to as R-113, and dichloropentafluoropropane as R-225 (a mixed product of $CF_3CF_2CHCl_2$ and $CF_2ClCF_2CHFCl$), gas chromatography as GC, and gas chromatography mass spectrometry as GC-MS. The results in the GC analyses are shown by the peak area ratios. The pressure is shown by a gauge pressure. $R^{F1}$ represents —$CF(CF_3)O(CF_2)_3F$, and $R^{F2}$ represents —$CF(CF_3)OCF_2CF(CF_3)O(CF_2)_3F$.

EXAMPLE 1

Production of fluoroadamantane-1-fluoride

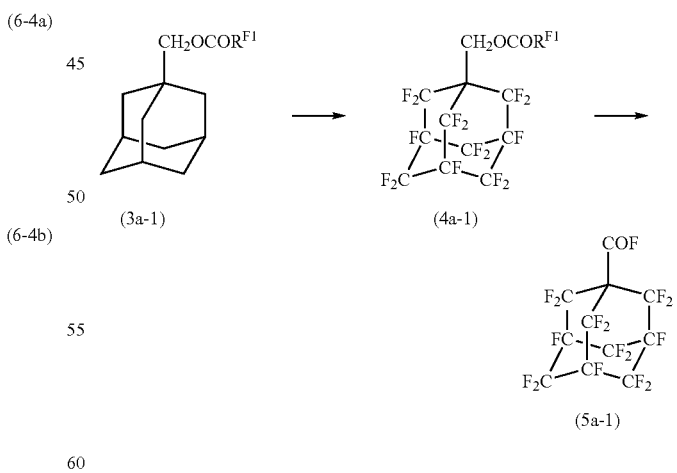

EXAMPLE 1-1

Preparation of compound (3a-1)

1-hydroxymethyladamantane (8 g) and $FCOR^{F1}$ (25.5 g) were reacted to obtain compound (3a-1) (20.4 g).

EXAMPLE 1-2

Preparation of compound (4a-1) (case 1)

Into a 500 mL autoclave made of nickel, R-113 (312 g) was introduced, stirred and maintained at 25° C. At a gas outlet of the autoclave, a condenser maintained at 25° C., a NaF pellet packed layer and a condenser maintained at 10° C. were installed in series. Further, a liquid-returning line was installed to return the condensed liquid from the condenser maintained at −10° C., to the autoclave. After blowing nitrogen gas for 1.0 hour, fluorine gas diluted to 20% with nitrogen gas (hereinafter referred to as 20% fluorine gas) was blown at a flow rate of 9.97 L/hr for one hour. Then, while 20% fluorine gas was supplied at the same flow rate, a solution having the compound (3a-1) (5.0 g) obtained in Example 1-1 dissolved in R-113 (102 g), was injected over a period of 4.7 hours.

Then, while 20% fluorine gas was supplied at the same flow rate and the pressure of the autoclave was maintained at 0.15 MPa, a R-113 solution having a benzene concentration of 0.01 g/ml (hereinafter referred to as the benzene solution) was injected in an amount of 9 ml while the internal temperature of the autoclave was raised from 25° C. to 40° C., whereupon the benzene inlet of the autoclave was closed, and stirring was continued for 0.3 hour. Then, while the autoclave pressure was maintained at 0.15 MPa and the autoclave internal temperature was maintained at 40° C., the benzene solution (6 ml) was injected, and stirring was continued for 0.3 hour. Then, while the autoclave pressure was maintained at 0.15 MPa and the autoclave internal temperature was maintained at 40° C., the benzene solution (8.5 ml) was injected, and stirring was further continued for 1.0 hour. The total amount of benzene injected was 0.24 g, and the total amount of R-113 injected was 23.5 ml. Further, nitrogen gas was blown for 1.0 hour. The desired product was quantified by $^{19}$F-NMR (internal standard: $C_6F_6$), whereby the yield of the compound (4a-1) as a completely fluorinated product was 29%. Further, a partially fluorinated product of the compound (3a-1) was formed in a yield of 71%.

EXAMPLE 1-3

Preparation of Compound (4a-1) (case 2)

The same autoclave as in Example 1-2 was prepared, and 20% fluorine gas was blown at a flow rate of 10.60 L/hr for one hour. While 20% fluorine gas was supplied at the same flow rate, a solution having the compound (3a-1) (5.0 g) obtained in Example 1-1 dissolved in R-113 (200 g), was injected over a period of 6.5 hours.

Then, while 20% fluorine gas was supplied at the same flow rate and the autoclave pressure was maintained at 0.15 MPa, a R-113 solution of compound (3a-1) (0.01 g/ml) was injected in an amount of 9 ml while the temperature was raised from 25° C. to 40° C., whereupon the benzene inlet of the autoclave was closed, and stirring was continued for 0.23 hour. Then, while the autoclave pressure was maintained at 0.15 MPa and the autoclave internal temperature was maintained at 40° C., the benzene solution (6 ml) was injected, and stirring was continued for 0.3 hour. Then, the same operation was carried out three times. Further, stirring was continued for 0.7 hour. The total amount of benzene injected was 0.35 g, and the total amount of R-113 injected was 33.0 ml. Further, nitrogen gas was blown for 1.0 hour. The desired product was quantified by $^{19}$F-NMR (internal standard: $C_6F_6$), whereby the yield of the compound (4a-1) was 61%.

EXAMPLE 1-4

Preparation of Compound (5a-1)

Compound (4a-1) (5.3 g) obtained in Example 1-3 was charged together with KF powder (0.3 g) into a flask and heated in an oil bath at from 80 to 90° C. for 4 hours with vigorous stirring. At the top of the flask, a reflux condenser adjusted at the temperature of 20° C. and a pack made of a fluorine resin film (Tedler Pack, tradename, manufactured by Du Pont) were installed in series. After cooling, a liquid sample (3.4 g) was recovered. As a result of the analyses by GC-MS and $^{19}$F-NMR, the liquid sample was confirmed to contain compound (5a-1) and $CF_3CF(OCF_2CF_2CF_3)COF$ as the main products.

$^{19}$F-NMR (376.0 MHz, solvent: $CDCl_3$, standard: $CFCl_3$) δ (ppm): 55.9 (1F), −110.0 (6F), −120.5 (6F), −218.9 (3F).

EXAMPLE 2

Production of 1-hydroxyfluoroadamantane

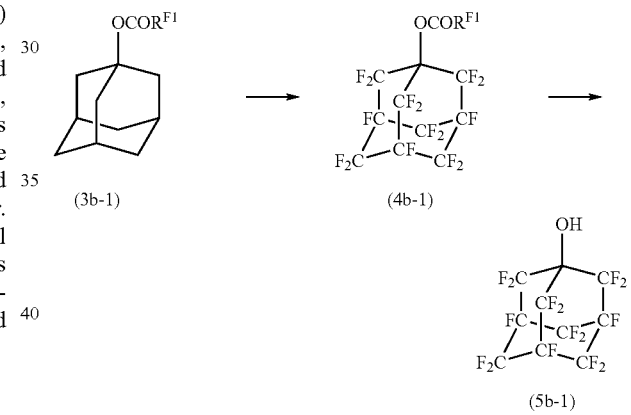

EXAMPLE 2-1

Production of Compound (3b-1)

1-hydroxyadamantane (3.09 g, 20.3 mmol) and $R^{F1}COF$ (9.94 g, 29.9 mmol) were reacted to obtain compound (3b-1) at a selectivity of 99.8% and in a yield of 93.2%.

EXAMPLE 2-2

Production of Compound (4b-1)

The same autoclave as in Example 1-2 was prepared, and after blowing 20% diluted fluorine gas at room temperature at a flow rate of 13.22 L/hr for 30 minutes, the internal pressure of the autoclave was raised to 0.15 MPa, whereupon the same gas was blown for further 30 minutes. Then, while 20% diluted fluorine gas was supplied at the same flow rate, a solution having compound (3b-1) (5 g) obtained in Example 2-1 dissolved in R-113 (100 g), was injected over a period of 4.2 hours.

A reaction was carried out under the same conditions as in Example 1-2 (provided that the benzene injection was carried out three times, and the total amount of benzene injected was 0.33 g, and the total amount of R-113 injected was 33 mL). After the reaction, the internal pressure of the reactor was adjusted to atmospheric pressure, and nitrogen gas was blown for one hour. The product was analyzed by $^{19}$F-NMR, whereby it was confirmed that compound (4b-1) was contained in a yield of 83%.

EXAMPLE 2-3

Production of Compound (5b-1)

The product (6.3 g) obtained in Example 2-2 was charged into a 50 mL round-bottomed flask, and an ethanol solution containing 10 wt % of sodium hydroxide was dropwise added with stirring in a water bath. The temperature was slowly raised to 50° C. while the stirring was continued, and after three hours, the stirring was stopped. Extraction was carried out three times by adding R-225, and the obtained organic layer was concentrated to recover a sample of white crystals (2.3 g). As a result of the analyses by GC-MS and $^{19}$F-NMR, it was confirmed that compound (5b-1) was the main product.

$^{19}$F-NMR (376.2 MHz, solvent: CDCl$_3$, standard: CFCl$_3$) δ (ppm): −116.5 to −125.0 (12F), −220.0 to −224.0 (3F).

Further, in the product, 2-hydro-1-hydroxyperfluoroadamantane i.e. a compound having one hydrogen atom bonded at 2-position (i.e. monohydrogenated) was contained.

$^{1}$H-NMR (300.4 MHz, solvent: CDCl$_3$, standard: TMS) δ (ppm): 5.24 (d, $J_{HF}$=48.1 Hz, 1H)

$^{19}$F-NMR (282.7 MHz, solvent: CDCl$_3$, standard: CFCl$_3$) δ (ppm): −119.2 to −125.2 (10F), −213.5 (1F), −222.4 (1F), −223.5 (1F), −224.8 (1F)

EXAMPLE 3

Production of fluoroadamantane-1-acylfluoride

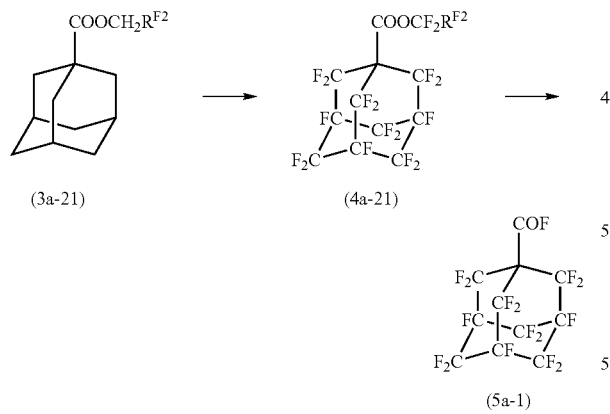

EXAMPLE 3-1

Production of Compound (3a-21)

Adamantane-1-acylfluoride (1.95 g, 9.8 mmol) and R$^{F2}$CH$_2$OH (4.61 g, 9.6 mmol) were reacted to obtain compound (3a-21) at a selectivity of 83.8% and in a yield of 74.4%.

EXAMPLE 3-2

Production of Compound (4a-21)

The same autoclave as in Example 1-2 was prepared, and 20% fluorine gas was blown at room temperature at a flow rate of 11.31 L/hr for 30 minutes. Then, the internal pressure of the autoclave was raised to 0.20 MPa, and then the same gas was blown for further 30 minutes.

Then, while the internal pressure of the reactor was maintained at 0.20 MPa, and 20% fluorine gas was blown at the same flow rate, a solution having compound (3a-21) (4 g) obtained in Example 3-1 dissolved in R-113 (80 g) was injected over a period of 3.3 hours.

Thereafter, a reaction was carried out in the same manner as in Example 1-2 except that the internal pressure of the autoclave was maintained at 0.20 MPa, injection of the benzene solution was repeated 5 times, and the total amount of benzene injected was 0.45 g, and the total amount of R-113 injected was 45 mL. After the reaction, the internal pressure of the reactor was adjusted to normal pressure, and nitrogen gas was supplied for one hour. The product was analyzed by $^{19}$F-NMR, whereby it was confirmed that compound (4a-21) was contained in a yield of 86%.

EXAMPLE 3-3

Production of Compound (5a-1)

Compound (4a-21) (4.8 g, 5.0 mmol) obtained in Example 3-2 was charged together with KF powder (0.09 g, 1.5 mmol) into a round-bottomed flask and heated in an oil bath at 140° C. for one hour with vigorous stirring. At the top of the flask, a reflux condenser having the temperature adjusted at 20° C., was installed, and in a receptacle portion, a liquid sample (3.2 g) was recovered. As a result of the analyses by GC and $^{19}$F-NMR, it was confirmed that compound (5a-1) and R$^{F2}$COF were the main products.

$^{19}$F-NMR (376.2 MHz, solvent: CDCl$_3$, standard: CFCl$_3$) δ (ppm): 55.9 (1F), −110.2 (6F), −120.6 (6F), −219.0 (3F)

EXAMPLE 4

Production of fluoroadamantane-1,3-diacylfluoride

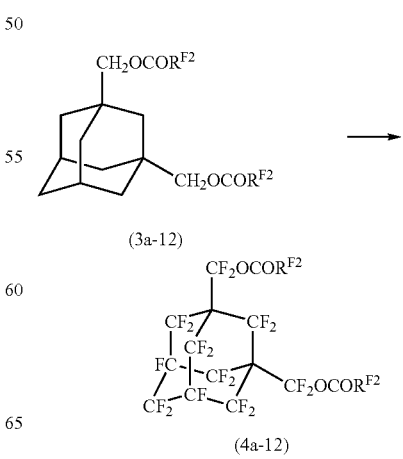

-continued

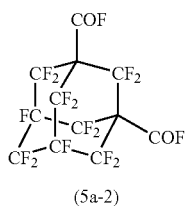

(5a-2)

EXAMPLE 4-1

Production of Compound (3a-12)

1,3-(bishydroxymethyl)adamantane (0.78 g) and $R^{F2}COF$ (5.74 g) were reacted to obtain compound (3a-12) at a selectivity of 99.7% and in a yield of 46%.

EXAMPLE 4-2

Production of Compound (4a-12)

The same autoclave as in Example 1-2 was prepared, and while the internal temperature of the autoclave was maintained at 25° C., nitrogen gas was blown for 1.0 hour. After blowing 20% fluorine gas at a flow rate of 9.05 L/hr for 30 minutes, the internal pressure of the autoclave was raised to 0.15 MPa, and the same gas was further blown for 30 minutes. Then, while 20% fluorine gas was supplied at the same flow rate, a solution having compound (3a-12) (2.46 g) obtained in Example 2-1 dissolved in R-113 (49.03 g), was injected over a period of 1.3 hours.

A reaction was carried out under the same conditions as in Example 1-2 (provided that the total amount of benzene injected was 0.34 g, and the total amount of R-113 injected was 33 mL). After the reaction, the internal pressure of the autoclave was adjusted to atmospheric pressure, and nitrogen gas was supplied for one hour.

The content of the autoclave was analyzed by GC-MS and NMR, whereby formation of compound (4a-12) (yield: 76%) and compound (4a-12H) as a 2-monohydro derivative of compound (4a-12), was confirmed.

EXAMPLE 4-3

Production of Compound (5a-2)

The mixture (2.39 g) obtained in Example 4-2 was charged together with KF powder (0.08 g) into a flask. At the top of the flask, a reflux condenser having the temperature adjusted at 20° C. and a pack made of a fluorine resin film (Tedler Pack, tradename, manufactured by Du Pont) were installed in series. While the interior of the flask was vigorously stirred, the flask was immersed in an oil bath of from 117 to 120° C. and heated for 3 hours. Then, the flask was cooled, and then, the KF powder was removed by filtration with a filter to recover a liquid sample (2.00 g).

The liquid sample was analyzed by GC, GC-MS and NMR, whereby formation of the above compound (5a-2) and compound (5a-2H) as a 2-monohydro derivative of compound (5a-2), was confirmed.

Compound (5a-2): $^{19}$F-NMR (283.7 MHz, solvent: CDCl$_3$, standard: CFCl$_3$) δ (ppm): 55.4(2F), −97.9(2F), −109.9 (8F), −120.8 (2F), −217.8 (2F)

Compound (5a-2H): $^1$H-NMR (300.4 MHz, solvent: CDCl$_3$, standard: TMS) δ (ppm): 5.95 (d, $J_{FH}$=42.3 Hz, 1H)

$^{19}$F-NMR (282.7 MHz, solvent: CDCl$_3$, standard: CFCl$_3$) δ (ppm): 49.4 (2F), −107.4 to −112.0 (8F), −120.8 (2F), −204.7 (1F), −217.8 to −218.4 (2F)

EXAMPLE 5

Production of fluoroadamantane-1,3,5,7-tetraacylfluoride

By changing 1,3-(bishydroxymethyl)adamantane in Example 5 to 1,3,5,7-(tetrakishydroxymethyl)adamantane, the reactions are carried out in the same manner as in Examples 4-1 to 4-3 to obtain perfluoroadamantane-1,3,5,7-tetraacylfluoride. In the product, 2-hydroperfluoroadamantane-1,3,5,7-tetraacylfluoride is contained.

EXAMPLE 6

Production of fluoroadamantane-1,3,5-tetraacylfluoride

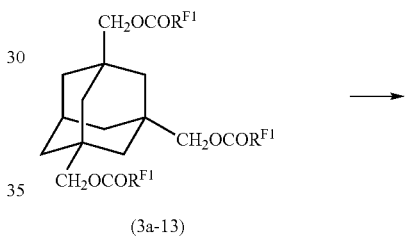

(3a-13)

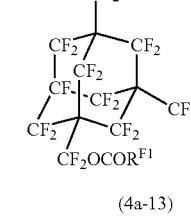

(4a-13)

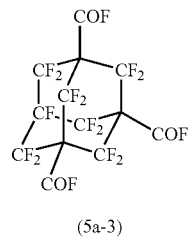

(5a-3)

EXAMPLE 6-1

Production of Compound (3a-13)

1,3,5-tris(hydroxymethyl)adamantane (22.27 g) obtained by reduction after converting carboxyl groups of 1,3,5-tricarboxyadamantane to carboxymethyl groups, was reacted with $R^{F1}COF$ (118.53 g) to obtain compound (3a-13) (106.22 g) in a yield of 93%.

EXAMPLE 6-2

Production of Compound (4a-13)

An autoclave (internal capacity: 3 L, made of nickel) was prepared, and at a gas outlet of the autoclave, a condenser maintained at 20° C., a NaF pellet packed layer and a condenser maintained at −10° C., were installed in series. Further, a liquid-returning line to return a condensed liquid from the condenser maintained at −10° C. to the autoclave, was installed.

Into the autoclave, R-113 (1,600 g) was charged and stirred at 25° C. Into the autoclave, nitrogen gas was blown at 25° C. for one hour, and then 20% fluorine gas was blown by nitrogen gas at 25° C. at a flow rate of 16.05 L/hr. Then, while 20% fluorine gas was supplied at the same flow rate, a liquid having compound (3a-13) obtained in Example 6-1 dissolved in R-113 (700 g), was injected over a period of 20.0 hours.

Then, while 20% fluorine gas was supplied at the same flow rate, the internal pressure of the autoclave was raised to 0.15 MPa, a R-113 solution having a benzene concentration of 6 mg/mL was injected in an amount of 110 mL under heating from 25° C. to 40° C., whereupon the benzene solution inlet of the autoclave was closed.

Further, while 20% fluorine gas was supplied at the same flow rate, stirring was continued for one hour. Then, the pressure in the reactor was adjusted to atmospheric pressure, and nitrogen gas was supplied for one hour. The content of the autoclave was analyzed by NMR, whereby formation of compound (4a-13) and compound (4a-13H) as a 2-monohydro derivative of compound (4a-3) was confirmed.

EXAMPLE 6-3

Production of Compound (5a-3)

Using the mixture obtained in Example 6-2, the same reaction as in Example 3-3 is carried out. The product is analyzed by GC-MS and NMR, whereby formation of the above compound (5a-3) and compound (5a-3H) as a 2-monohydro derivative of compound (5a-3) is confirmed.

EXAMPLE 7

Production of 1-acryloyloxy(fluoroadamantane)

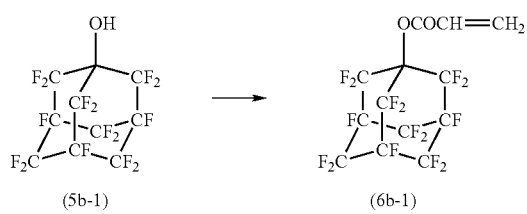

EXAMPLE 7-4

Production of Compound (6b-1)

The powder (1.1 g) of 1-hydroxyperfluoroadamantane obtained in Example 2-3 was charged into a 50 mL round-bottomed flask, and diethyl ether (2.5 g) and triethylamine (0.2 g) were added. This flask was immersed in ice bath, and acrylic acid chloride (0.16 g) was slowly dropwise added with stirring. At the same time as dropwise addition, white precipitate formed in the flask. After the dropwise addition of the acrylic acid chloride in the entire amount, the ice bath was removed, and stirring was continued at 25° C. for 10 hours. This reaction solution was washed with deionized water to remove the formed white precipitate thereby to separate the organic layer. As a result of the analyses by GC, GC-MS and 19F-NMR, formation of compound (6b-1) and compound (6b-1H) as a 2-monohydro derivative of compound (6b-1) was confirmed. As obtained from GC, the conversion for compound (6b-1) was 56%, the conversion for (6b-1H) was 97%, the selectivity for compounds (6b-1) and (6b-1H) together was 93%.

Compound (6b-1): $^1$H-NMR (300.4 MHz, solvent: CDCl$_3$, standard: TMS) δ (ppm): 6.08(dd, $J_{HF}$=1.5, 10.2 Hz, 1H), 6.25 (dd, $J_{HF}$=10.2, 16.5 Hz, 1H), 6.57(dd, $J_{HF}$=1.5, 16.5 Hz, 1H). $^{19}$F-NMR (282.7 MHz, solvent: CDCl$_3$, standard: CFCl$_3$) δ (ppm): −114.7 (6F), −121.2 (6F), −221.6 (3F)

Compound (6b-1H): $^1$H-NMR (300.4 MHz, solvent: CDCl$_3$, standard: TMS) δ (ppm): 6.16 (dd, $J_{HF}$=1.5, 10.5 Hz, 1H), 6.24 (dd, $J_{HF}$=10.5, 16.2 Hz, 1H), 6.64 (dd, $J_{HF}$=1.5, 16.2 Hz, 1H), 6.7 7(dq, $J_{HF}$=45.4, 6.3 Hz, 1H). $^{19}$F-NMR (282.7 MHz, solvent: CDCl$_3$, standard: CFCl$_3$) δ (ppm): −113.4 to −124.8 (10F), −212.5 (1F), −222.2 (2F), −222.9 (1F).

EXAMPLE 8

Production of 1,3-dihydroxy(fluoroadamantane) and its Acryloyl Derivative

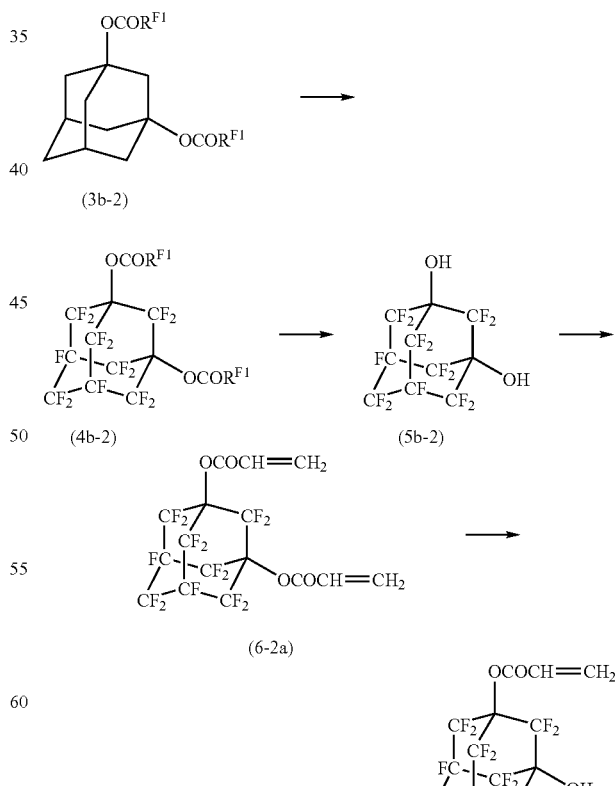

EXAMPLE 8-1

Production of Compound (3b-2)

3-adamantane diol (2.01 g, 11.9 mmol) and $R^{F1}COF$ (11.23 g, 33.8 mmol) were reacted to obtain compound (3b-2) at a selectivity of 95.4% and in a yield of 83.4%.

EXAMPLE 8-2

Production of Compound (4b-2)

The same autoclave as in Example 1-2 was prepared. Nitrogen gas was blown at room temperature for one hour, then 20% fluorine gas was blown at room temperature at a flow rate of 10.6 L/hr for 30 minutes, and then the internal pressure of the autoclave was raised to 0.15 MPa, and the same gas was further blown for 30 minutes. Then, while the internal pressure of the reactor was maintained at 0.15 MPa, and 20% fluorine gas was blown at the same flow rate, a solution having the product (4.7 g) obtained in Example 8-1 dissolved in R-113 (94.3 g), was injected over a period of 2.6 hours.

Then, while 20% fluorine gas was blown at the same flow rate, and the internal pressure of the autoclave was maintained at 0.15 MPa, a R-113 solution having a benzene concentration of 0.01 g/mL was injected in a amount of 9 mL while the temperature was raised from 25° C. to 40° C., whereupon the benzene solution inlet of the autoclave was closed, and stirring was continued for 0.3 hour.

Then, while the internal pressure of the reactor was maintained at 0.15 MPa, and the internal temperature of the reactor was maintained at 40° C., the above benzene solution (6 mL) was injected, whereupon the benzene solution inlet of the autoclave was closed, and stirring was continued for 0.3 hour. Further, the same operation was repeated three times. The total amount of benzene injected was 0.34 g, and the total amount of R-113 injected was 33 mL.

Further, while 20% fluorine gas was blown at the same flow rate, stirring was continued for one hour. Then, the internal pressure of the reactor was adjusted to atmospheric pressure, and nitrogen gas was blown for one hour. The product was analyzed by GC-MS and NMR, whereby formation of compound (4b-2) (yield: 55%) and compound (4b-2H) (yield: 27%) as a 2-monohydro derivative of compound (4b-2) was confirmed.

EXAMPLE 8-3

Production of Compound (5b-2)

The solution (11.8 g) of the product obtained in Example 8-2 was charged into a 100 mL round-bottomed flask, and a 15 wt % methanol solution (24 g) of sodium hydroxide was dropwise added. The mixture was heated with stirring and refluxed for 11 hours, and then it was left to cool. A dilute HCl aqueous solution was slowly dropwise added until the liquid became neutral, and then, t-butyl methyl ether was added and extraction was carried out three times. The obtained organic layer was concentrated by an evaporator and further sufficiently evaporated to dryness by a vacuum pump to recover a pale yellow powder (3.8 g). As a result of the analysis by $^{19}$F-NMR, formation of compound (5b-2) and compound (5b-2H) as a 2-monohydro derivative of compound (5b-2) was confirmed.

Compound (5b-2): $^{19}$F-NMR (282.7 MHz, solvent: $CD_3OD$, standard: $CFCl_3$) δ (ppm): −117.6 to −124.4, −221.5 to −224.5.

Compound (5b-2H): $^1$H-NMR (300.4 MHz, solvent: $CDCl_3$, standard: TMS) δ (ppm): 4.95 (dm, $J_{HF}$=47.8Hz, 1H). $^{19}$F-NMR (282.7 MHz, solvent: $CD_3OD$, standard: $CFCl_3$) δ (ppm): −118.1 to −123.9 (10F), −221.6 (1F), −222.5 (1F), −223.5 (dm, J=48 Hz, 1F).

EXAMPLE 8-4

Production of Compound (6-2a)

The pale yellow powder (3.9 g) obtained in Example 8-3 was charged into a 100 mL round-bottomed flask, and t-butyl methyl ether (30 mL) and triethylamine (2.03 g) were added. This flask was immersed in ice bath, and acrylic acid chloride (1.63 g) was slowly dropwise added with stirring. At the same time as the dropwise addition, white crystal formed in the flask. After acrylic acid chloride was dropwise added in the entire amount, the ice bath was removed, and stirring was continued at 25° C. for 19 hours. A part of this reaction solution was taken and concentrated and then subjected to a NMR analysis, whereby formation of compound (6-2a) and compound (6b-2aH) as a 2-monohydro derivative of compound (6-2a), was confirmed. Further, formation of (6-1b) and compound (6-1bH) as a 2-monohydro derivative of compound (6-1b) was confirmed. The conversion for compound (6-1b) was 56%, the conversion for compound (6-1bH) was 97%, and the selectivity for compound (6-1b) and (6-1bH) together was 93%.

$^1$H-NMR (300.4 MHz, solvent: $CDCl_3$, standard: TMS) δ (ppm): 6.09 to 6.73 (m), 8.02 (dot, J=42, 6.6Hz). $^{19}$F-NMR (282.7 MHz, solvent: $CDCl_3$, standard: $CFCl_3$) δ (ppm): −113.5 to 121.8 (m), −219.6 (m), −221.1 (m), −221.5 (m).

EXAMPLE 9

Production of 1,3,5-trihydroxyfluoroadamantane and its Acryloyl Derivative

EXAMPLE 9-1

Production of 1,3,5-tris(perfluoroisobutyloyloxy)adamantane 1,3,5-trihydroxyadamantane (5.15 g) and perfluoroisobutyloyl fluoride (86 g) were reacted and recrystallized, whereby colorless crystal of 1,3,5-tris(perfluoroisobutyloyloxy)adamantane was obtained at a recovery rate of 50%.

EXAMPLE 9-2

Production of 1,3,5-tris(perfluoroisobutyloyloxy)adamantane

The same autoclave as in Example 1-2 was prepared. Nitrogen gas was blown into the autoclave at 25° C. for one hour, and then, 20% fluorine gas was blown at 25° C. at a flow rate of 5.47 L/hr for one hour. Then, while 20% fluorine gas was blown at the same flow rate, a solution having crystal (5 g) of 1,3,5-tri(perfluoroisobutyloyloxy)adamantane obtained in Example 9-1 dissolved in R-113 (100 g), was injected over a period of 2.8 hours.

Then, while 20% fluorine gas was blown at the same flow rate, and the pressure of the reactor was maintained at 0.15 MPa, a R-113 solution having a benzene concentration of 0.01 g/mL was injected in an amount of 9 mL while the temperature was raised from 25° C. to 40° C., whereupon the benzene solution inlet of the autoclave was closed, and stirring was continued for 0.3 hour.

Then, while the internal pressure of the reactor was maintained at 0.15 MPa, and the internal temperature of the reactor was maintained at 40° C., the above benzene solution was injected in an amount of 6 mL, whereupon the benzene solution inlet of the autoclave was closed, and stirring was continued for 0.3 hour. Further, the same operation was repeated three times. The total amount of benzene injected was 0.33 g, and the total amount of R-113 injected was 33 mL.

Further, while 20% fluorine gas was blown at the same flow rate, stirring was continued for one hour. Then, the internal pressure of the reactor was adjusted to atmospheric pressure, and nitrogen gas was blown for one hour. The product was analyzed by NMR and GC, whereby formation of perfluoro (1,3,5-tri(isobutyloyloxy)adamantane) (selectivity: 4%) and 2-hydro-1,3,5-tri(perfluoroisobutyloyloxy)adamantane (selectivity: 80%) was confirmed.

EXAMPLE 9-3

Production of perfluoro(1,3,5-trihydroxyadamantane)

The product obtained in Example 9-2 was concentrated and added to an ethanol solution (70 mL) of sodium hydroxide (5 g), and precipitated solid was dissolved in R-225 and refluxed under heating for 5 hours. After stirring at 25° C. for 19 hours, refluxing under heating was carried out for further 7 hours. After being left to cool, the reaction solution was concentrated to obtain an orange-colored solid-liquid mixture. It was neutralized with 3M hydrochloric acid, washed with R-225 and then, the aqueous layer was concentrated and after removing water completely, extracted with ethanol. The extract solution was concentrated to obtain a solid (0.8 g). The solid was analyzed, whereby formation of 1,3,5-trihydroxyperfluoroadamantane and 2-hydro-1,3,5-trihydroxy-perfluoroadamantane, was confirmed.

1,3,5-trihydroxyperfluoroadamantane: $^{19}$F-NMR (282.7 MHz, solvent: CD$_3$OD, standard: CFCl$_3$) δ (ppm): −117.2 to −124.4 (m), −220.6 to −222.2 (m).

2-hydro-1,3,5-trihydroxy-perfluoroadamantane: $^1$H-NMR (300.4 MHz, solvent: CD$_3$OD, standard: CD$_3$OD) δ (ppm): 3.7. $^{19}$F-NMR (282.7 MHz, solvent: CD$_3$OD, standard: CFCl$_3$) δ (ppm): −117.2 to −124.4 (m), −220.5 (m), −221.5 (m), −223.4 (m).

EXAMPLE 9-4

Production of 1,3,5-triacryloyloxy(perfluoroadamantane)

The product (0.42 g) obtained in Example 9-3 was stirred in diethyl ether (10 mL) and cooled with ice water, and then triethylamine (0.42 g) and acryloyl chloride (0.33 g) were added. Then, the mixture was stirred at 25° C. overnight, then solid was filtered off. Then, the filtrate was concentrated, and the residue was separated by column chromatography to obtain a product (0.06 g). The product was analyzed, whereby formation of 1,3,5-triacryloyloxy(perfluoroadamantane) and 2-hydro-1,3,5-triacryloyloxy(perfluoroadamantane) was confirmed.

1,3,5-triacryloyloxy(perfluoroadamantane): $^1$H-NMR (300.4 MHz, solvent: CDCl$_3$, standard: TMS) δ (ppm): 6.06 to 6.65 (m). $^{19}$F-NMR (282.7 MHz, solvent: CDCl$_3$, standard: CFCl$_3$) δ (ppm): −112.3 to −121.9 (m), −219.2 (m).

2-hydro-1,3,5-triacryloyloxy(perfluoroadamantane): $^1$H-NMR (300.4 MHz, solvent: CDCl$_3$, standard: TMS) δ (ppm): 6.06 to 6.65 (m). $^{19}$F-NMR (282.7 MHz, solvent: CDCl$_3$, standard: CFCl$_3$) δ (ppm): −112.3 to −121.9 (m), −219.4 (m), −220.3 (m), −220.8 (m).

EXAMPLE 9-5

Acryloyl conversion of 1,3,5-trihydroxy(fluoroadamantane)

The product (0.26 g) obtained in Example 9-3 was stirred in diethyl ether (5 mL) and cooled with ice water, and then triethylamine (0.34 g) and acryloyl chloride (0.089 g) were added. Then, the mixture was stirred at 25° C. overnight, and solid was filtered off, and then the filtrate was concentrated. The residue was separated by column chromatography to obtain a product (0.06 g).

The product was analyzed, whereby formation of 1-acryloyloxy-3,5-dihydroxy(perfluoroadamantane) and 1,3-diacryloyloxy-5-hydroxy(perfluoroadamantane) was confirmed. Further, formation of 2-hydro-1-acryloyloxy-3,5-dihydroxy(perfluoroadamantane) and 2-hydro-1,3-diacryloyloxy-5-hydroxy(perfluoroadamantane) was also confirmed.

1-acryloyloxy-3,5-dihydroxy(perfluoroadamantane): $^1$H-NMR (300.4 MHz, solvent: CDCl$_3$, standard: TMS) δ (ppm): 6.08 (dm, J=10.5 Hz), 6.21 (dd, J=10.5, 16.9 Hz), 6.51 (dm, J=16.9 Hz). $^{19}$F-NMR (282.7 MHz, solvent: CDCl$_3$, standard: CFCl$_3$) δ (ppm): −115.3 to −122.5 (m), −221 to −222 (m).

2-hydro-1-acryloyloxy-3,5-dihydroxy(perfluoroadamantane): $^1$H-NMR (300.4 MHz, solvent: CDCl$_3$, standard: TMS) δ (ppm): 6.08 (dm, J=10.5 Hz), 6.21 (dd, J=10.5, 16.9 Hz), 6.34 (dm, J=48 Hz), 6.51 (dm, J=16.9 Hz). $^{19}$F-NMR (282.7 MHz, solvent: CDCl$_3$, standard: CFCl$_3$) δ (ppm): −112.7 to −125.7 (m), −221.7 (m) to −222.5 (m).

3-diacryloyloxy-5-hydroxy(perfluoroadamantane): $^1$H-NMR (300.4 MHz, solvent: CDCl$_3$, standard: TMS) δ (ppm): 6.06 to 6.65 (m). $^{19}$F-NMR (282.7 MHz, solvent: CDCl$_3$, standard: CFCl$_3$) δ (ppm): −111.9 to −121.9(m), −218.8 to −222.3 (m).

2-hydro-1,3-diacryloyloxy-5-hydroxy(perfluoroadamantane): $^1$H-NMR (300.4 MHz, solvent: CDCl$_3$, standard: TMS) δ (ppm): 6.06 to 6.65 (m) $^{19}$F-NMR (282.7 MHz, solvent: CDCl$_3$, standard: CFCl$_3$) δ (ppm): −113.6 to −121.9 (m), −219.4 (m), −220.5 (m), −222.1 (m).

EXAMPLE 10

Production of 1,3,5,7-tetraacryloyloxy(fluoroadamantane)

By changing 1,3,5-trihydroxyadamantane in Example 9 to 1,3,5,7-tetrahydroxyadamantane, reactions are carried out in the same manner as in Examples 9-1 to 9-3 to obtain 1,3,5,7-tetrahydroxy(perfluoroadamantane).

Further, by carrying out the same reaction as in Example 9-4, 1,3,5,7-tetraacryloyloxy(perfluoroadamantane) is obtained.

The entire disclosures of Japanese Patent Application No. 2002-359471 filed on Dec. 11, 2002, Japanese Patent Application No. 2004-178330 filed on Jun. 16, 2004 and Japanese Patent Application No. 2004-178331 filed on Jun. 16, 2004 including specifications, claims and summaries are incorporated herein by reference in their entireties.

What is claimed is:

1. A compound of the following formula (5a'):

$$A^f(-COF)_n \quad (5a')$$

wherein $A^f$ is a n-valent adamantane group, A, in which n hydrogen atoms in adamantane are converted to connecting bonds, at least one hydrogen atom in group A is substituted by a fluorine atom, and n is an integer of from 2 to 4.

2. The compound according to claim 1, wherein $A^f$ is a group having all hydrogen atoms in the group A substituted by fluorine atoms.

3. The compound according to claim 1, wherein the hydrogen converted to a connecting bond is one bonded to a tertiary carbon atom.

4. The compound according to claim 1, wherein $A^f$ is a group having at least 50% of hydrogen atoms in the group A substituted by fluorine atoms.

5. The compound according to claim 1, wherein $A^f$ is a group having at least 90% of hydrogen atoms in the group A substituted by fluorine atoms.

6. The compound according to claim 1, wherein the compound is represented by one of the following formulae:

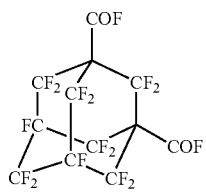
(5a-2)

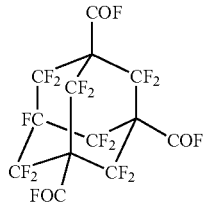
(5a-3)

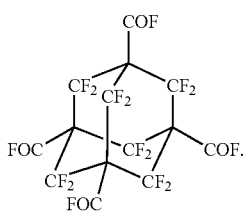
(5a-4)

7. The compound according to claim 1, wherein the compound is represented by the following formula, 5a-2:

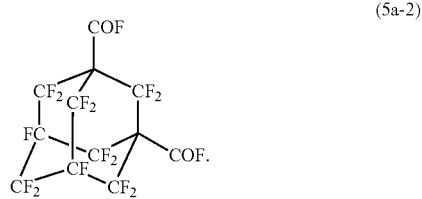
(5a-2)

8. The compound according to claim 1, wherein the compound is represented by the following formula, 5a-3:

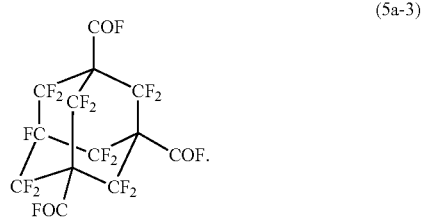
(5a-3)

9. The compound according to claim 1, wherein the compound is represented by the following formula, 5a-4:

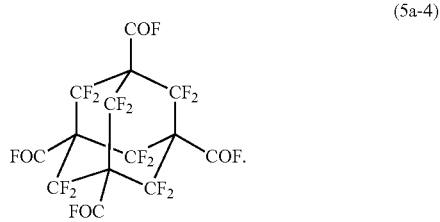
(5a-4)

* * * * *